United States Patent [19]
Qi et al.

[11] Patent Number: 5,661,037
[45] Date of Patent: Aug. 26, 1997

[54] METHOD OF DETECTING TAUTOMERIC CYCLIC 1,2-DIONES

[76] Inventors: Jian Steven Qi, 251 Kenville Rd. Apt # C, Buffalo, N.Y. 14215; David E. Albright, 6875 Plaza Dr. Apt# 3, Niagara Falls, N.Y. 14304; Garra C. Lester, 2346 New Jerusalem Rd., Eden, N.Y. 14057

[21] Appl. No.: 660,993

[22] Filed: Jun. 10, 1996

[51] Int. Cl.$^6$ .................................................. G01N 21/64
[52] U.S. Cl. ............................ 436/128; 436/163; 436/164
[58] Field of Search ............................... 436/127, 128, 436/163, 164

[56] References Cited

U.S. PATENT DOCUMENTS

| | | | |
|---|---|---|---|
| 4,045,487 | 8/1977 | Cleeland, Jr. et al. | 436/172 |
| 5,494,827 | 2/1996 | Oh et al. | 436/172 |

*Primary Examiner*—Jeffrey Snay
*Attorney, Agent, or Firm*—Richard D. Fuerle; Arthur S. Cookfair

[57] ABSTRACT

Disclosed is a method of determining whether a solvent contains a tautomeric cyclic 1,2-dione. It is first determined whether the pH of the solvent is acidic (<5), basic (>9), or neutral (5 to 9). If the pH is neutral, an acid or a base is added to make the pH acidic or basic, respectively. The UV absorbance at a first wavelength between about 230 nm and about 270 nm and at a second wavelength between about 280 and about 320 nm is determined. If the pH is acid, it is changed to basic and, if it is basic, it is changed to acidic. The UV absorbance at the first and second wavelengths is again determined. The presence of a tautomeric cyclic 1,2-dione is indicated if the absorbance at the first wavelength was greater when the solvent was acidic and the absorbance at the second wavelength was greater when the solvent was basic. The concentration of the tautomeric cyclic 1,2-dione can be determined by multiplying the change in absorbance by a constant.

17 Claims, 4 Drawing Sheets

METHOD OF DETECTING TAUTOMERIC CYCLIC 1,2-DIONES

CROSS-REFERENCE TO RELATED APPLICATION

This application is related to copending application Ser. No. 647,289 filed May 9, 1996, by David E. Albright and Edward A. Dietz, titled "Method For Reducing UV Absorption in Ethylene Glycols, Water, and Mixtures."

BACKGROUND OF THE INVENTION

This invention relates to a method of detecting the presence of a tautomeric cyclic 1,2-dione dissolved in a solvent such as ethylene glycol. In particular, it relates to detection of the dione by measuring the pH of the solvent, determining the UV absorption at 260 and 290 nm, then changing the pH from acidic to basic or basic to acidic, and again determining the UV absorption at those wavelengths.

Ethylene glycol has many uses, including as antifreeze and as a component for making polyesters such as poly (ethylene terephthalate). Ethylene glycol that is used to make polyesters must be very pure, which is usually indicated by a low concentration of aldehydes and a high UV transmission, typically tested at 220 nm, 250 nm, and 275 nm. High absorption at these wavelengths usually indicates the presence of undesirable impurities that lower polyester quality. The absorbance at 220 nm is generally associated with the presence of organic acids, such as formic acid, and conjugated aldehydes, such as acrolein and crotonaldehyde, which are produced during glycol manufacturing. The compounds responsible for absorbances at 250 and 275 nm are not specifically known, although they also originate from the glycol manufacturing process.

Ethylene glycol that does not meet UV absorbance specifications must be treated or reworked before it can be used to manufacture polyesters. One method of reducing UV absorbance is to pass the ethylene glycol through activated carbon to remove the impurities. While this procedure is often effective for low levels of the impurities, the carbon must be periodically replaced or regenerated, a significant expenditure in capital and operating costs for a large plant. Furthermore, for high levels of impurities, the carbon method may not have sufficient capacity. Thus, various other process improvements are being explored.

It has recently been discovered (see above-cited cross-referenced application, herein incorporated by reference) that cyclic diones are largely responsible for UV absorption at 250 to 275 nm in ethylene glycol.

However, until now, there has been no simple and practical analytical technique for determining whether or not these cyclic diones are present in various ethylene glycols and plant streams. Without such a method, tracing these compounds in glycol plants and making process improvements to remove them is difficult.

SUMMARY OF THE INVENTION

We have discovered a method for detecting the presence of tautomeric cyclic 1,2-diones in solution and determining their concentrations. The analytical test of this invention is very simple and easy to perform. It is based on our discovery that the absorbance of the tautomers at 290 nm increases (or transmission falls) when the pH goes from acidic to basic while the absorbance at 260 nm decreases (or transmission rises), and vice versa. Since there may be some other UV absorbers in the 260 and 290 nm range, directly using the absorbance at these wavelengths to indicate the presence of the cyclic dione is difficult. However, the change in absorbance in these wavelengths when the pH changes is characteristic of tautomeric cyclic 1,2-diones. The analytical test of this invention is very sensitive and is capable of detecting the presence of tautomeric cyclic 1,2-diones at levels of as little as 0.1 ppm or less.

DESCRIPTION OF THE PREFERRED EMBODIMENT

Figure 1:
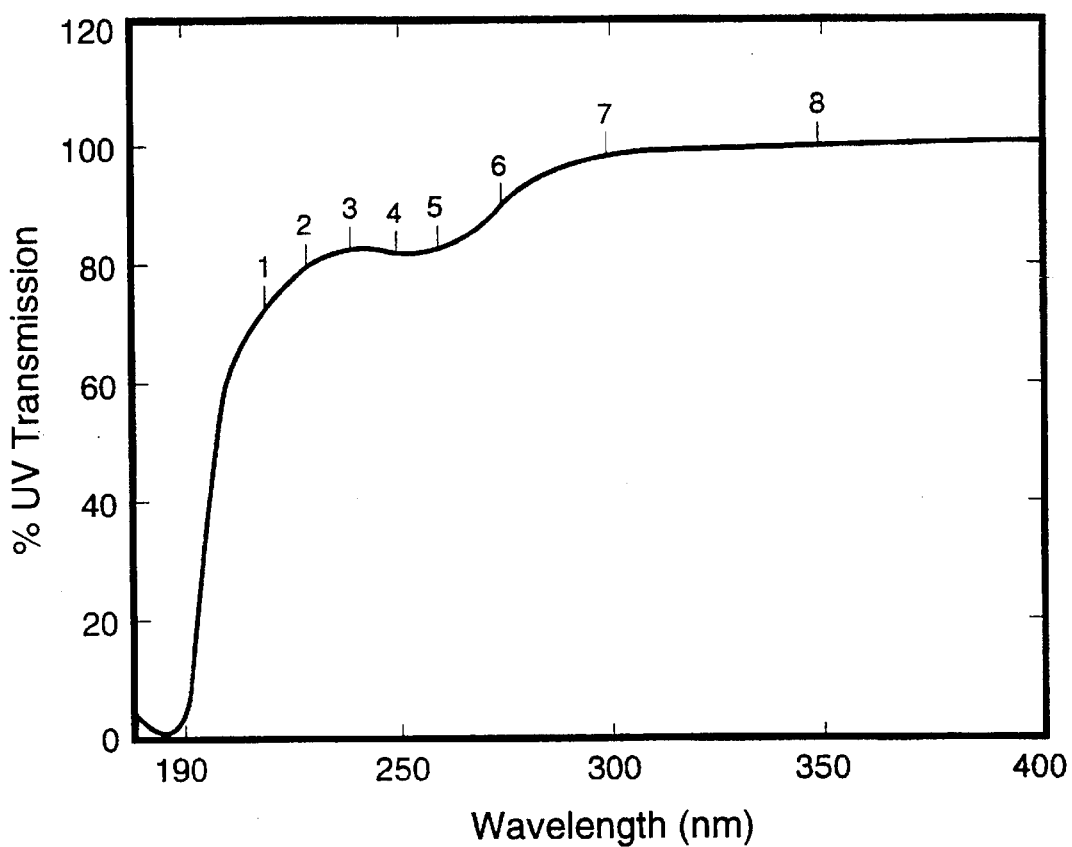
FIGS. 1 to 3 are graphs showing percent transmission at various wavelengths and are explained in more detail in the Examples that follow.

The analytical technique of this invention for detecting and quantifying the presence of tautomeric 1,2-diones can be applied to any solution in which they are dissolved. Any solvent that does not interfere with the UV measurements can form the solution including, for example, most organic solvents, (e.g., methylene chloride, alcohols and glycols, and even water.) However, the invention is most useful when the tautomers are dissolved in a glycol such as monoethylene glycol (MEG), diethylene glycol, or triethylene glycol.

The tautomeric cyclic 1,2-diones detectable by the method of this invention can have either 5-membered or 6-membered carbocyclic rings. They form 1,2-dione and enol tautomers as illustrated by the following equilibrium:

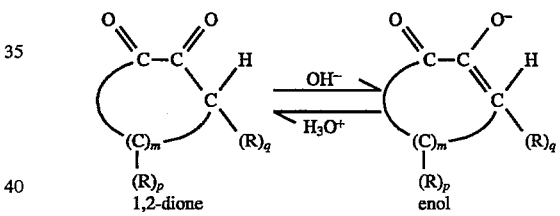

In the formulas, each R is independently selected from hydrogen and alkyl from $C_1$ to $C_{15}$, "m" is 2 or 3, q is 0 or 1, and p+q is 0 to 3 when "m" is 2 and 0 to 4 when "m" is 3. The 1,2-dione tautomer is formed at an acidic pH and the enol tautomer, which may exist as an anion, is formed at a basic pH. A tautomeric cyclic 1,2-dione, 3-methyl-1,2-cyclopentane dione, is an impurity in ethylene glycol and is a strong UV absorber at 260 nm; its enol tautomer, 2-hydroxy-3-methyl-cyclopentenone (HMCP), exists under basic conditions:

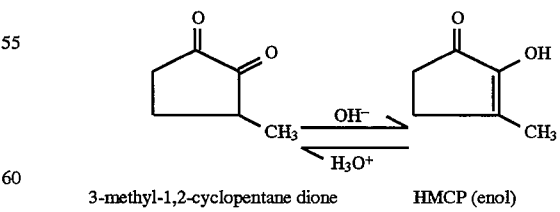

3-methyl-1,2-cyclopentane dione     HMCP (enol)

HMCP is known as "maple lactone" because it is used as a flavoring in artificial maple syrup. While we do not wish to be bound by any theories, we believe that when sodium hydroxide is added to the dione tautomer, the anion of HMCP is formed.

In the first step of the process of this invention, the sample to be analyzed is measured for UV transmission at wavelengths from 240 to 300 nm. A transmission less than 100% at 260 or 290 nm indicates the possible presence of the tautomeric cyclic 1,2 dione or HMCP. In such a case, the pH of the sample is determined. This can be accomplished by any conventional analytical technique for pH measurements. If the sample is near neutral or only slightly acidic or basic (pH5-9), an acid or a base is added to make the sample more acidic (pH<5) or more basic (pH>9). If the sample is already in the acidic or basic range, no adjustment is needed. Preferably, the pH should be adjusted to either between 1 and 4 or between 10 and 13, although slightly overdosed to more acid or more basic is acceptable. The acid or base used must not interfere with the UV transmission. In other words, the reagent must not itself a UV absorber or contains UV absorbing impurities in the 240 to 300 nm range. Suitable acids include sulfuric acid and hydrochloric acid and suitable bases include sodium hydroxide and potassium hydroxide.

After the pH adjustment, the second step of the process is performed, in which the UV absorbance of the adjusted sample is measured at 260 and 290 nm, respectively, using a UV spectrometer. The significant presence of the tautomeric cyclic 1,2-diones is indicated by a strong absorbance either at 260 nm for acidic pH or at 290 nm for basic pH.

In the third step, the pH of the sample is adjusted again, either from acidic to basic or basic to acidic, depending on the previous pH value. For example, if the previous pH is between 1–4, the pH now should be increased to 10–13, and vice versa. The adjusted sample is again measured for its UV absorbance at 260 and 290 nm. If a tautomeric cyclic 1,2-dione is present, when the pH is changed from acidic to basic the 260 nm absorbance measured will become lower than that obtained in the second step whereas the 290 nm absorbance will be higher. If the pH is changed from basic to acidic, the reverse is true, i.e., the 260 nm absorbance will increase while the 290 nm absorbance will decrease.

The pH of the sample can be once again adjusted back and the absorbance will return to that obtained in the second step. This change of absorbance at 260 and 290 nm when pH is adjusted from acidic to basic or from basic to acidic can be repeated as many times as desired.

The change in the 260 nm absorbance is proportional to the dione concentration while the change in the 290 nm absorbance is proportional to the enol concentration. Since the absorbances reflect a single compound in two tautomeric states, their concentrations theoretically should be equal. But in practice they may differ slightly and their average is used. The constant of proportionality can be determined by calibration using standards with known amounts of the tautomers, i.e., by measuring the change in UV absorbance at 260 and 290 nm corresponding to each pH adjustment using a sample of known concentration. The proportionality for the dione is obtained by dividing the known concentration by the change in the 260 nm absorbance, whereas the proportionality for enol is by the change in the 290 nm absorbance, as shown by Example 5.

The presence of a tautomeric cyclic 1,2-dione can be detected using the technique of this invention at any concentration down to as low as about 0.1 ppm. A typical concentration range encountered in the production of ethylene glycol is about 0.1 to 1 ppm. Note that since the UV absorbance is directly related to UV transmission, all the absorbance measurements described above can be substituted by transmission measurements.

The following examples further illustrate this invention.

EXAMPLE 1

Figure 2:
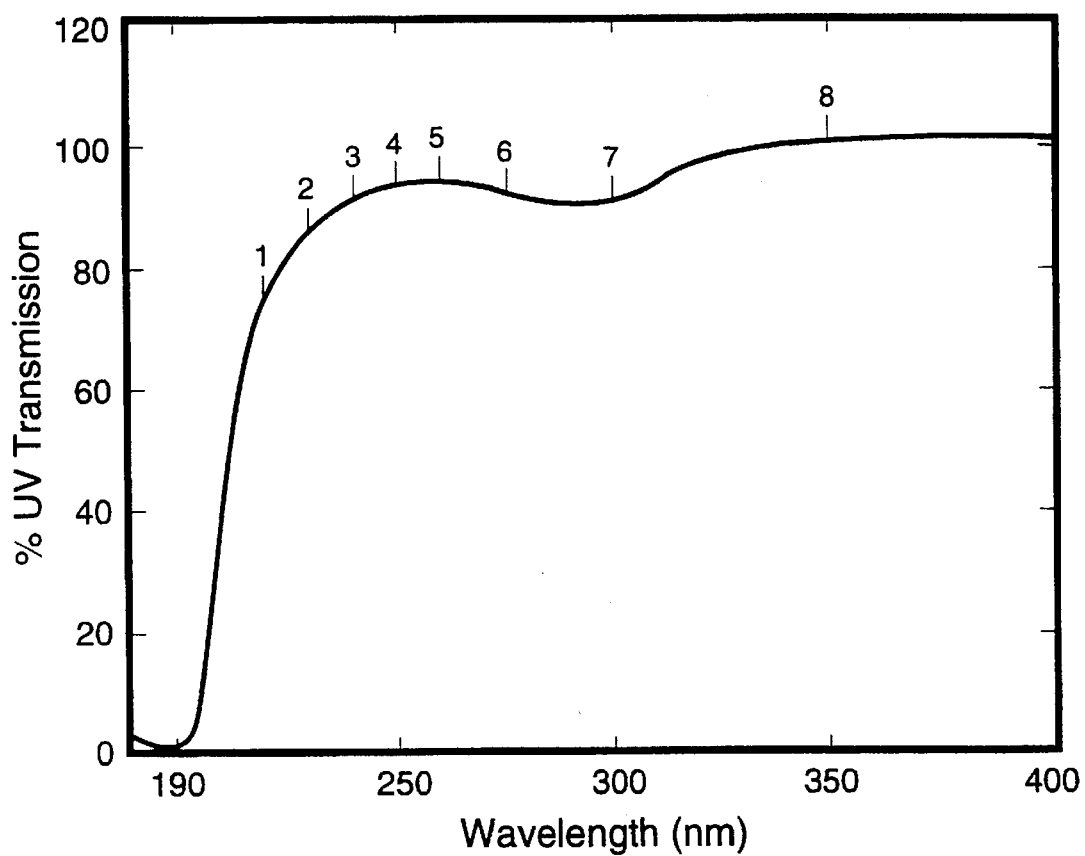

FIG. 1 is a UV transmission scan of a commercial fiber grade monoethylene glycol (MEG) having a pH of about 6 or 7 that contained less than 1 ppm HMCP as identified by gas chromatography-mass spectrometry (GC-MS). Absorbance at 260 nm was indicated by the dip in the transmission scan. After adding 250 ppm NaOH, the absorbance shifted to 290 nm, as shown in FIG. 2, which is a UV transmission scan obtained 2 hours after adding the NaOH at room temperature. We found that for this sample of MEG, 125 ppm NaOH resulted in the same effect as 250 ppm. When the MEG was heated above 50° C., a severe UV depression at all wavelengths occurred as a result of MEG decomposition.

EXAMPLE 2

Figure 3:
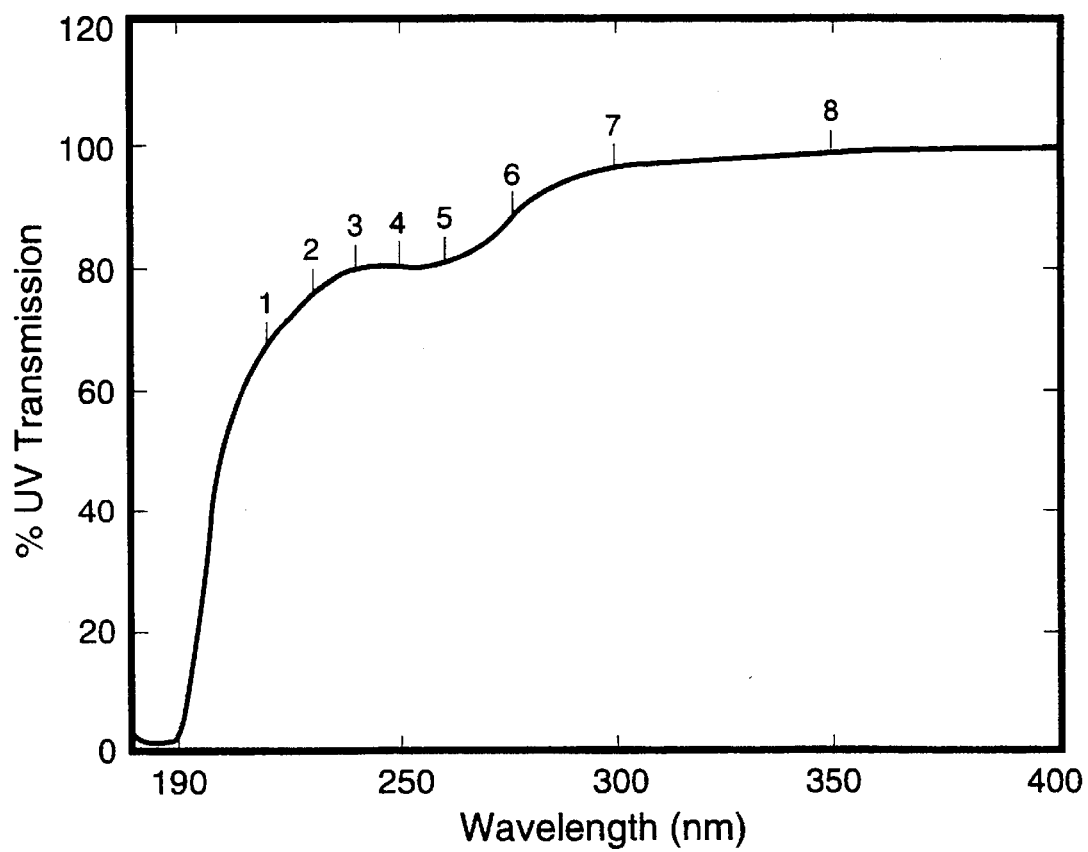

The 290 nm UV dip described in Example 1 and shown in FIG. 2 disappeared after the NaOH initially added was neutralized. FIG. 3 is a UV scan after neutralization using equivalent HCl. (The use of $H_2SO_4$ had the same effect.) The neutralization clearly shifted the FIG. 2 pattern back to the FIG. 1 pattern. The FIG. 2 pattern was then recreated again by another addition of NaOH.

In FIGS. 1, 2, and 3, the numbers indicate the wavelengths measured: 1 at 220 nm, 2 at 230 nm, 3 at 240 nm, 3 at 250 nm, 5 at 260 nm, 6 at 275 nm, 7 at 300 nm, and 8 at 350 nm. FIGS. 1 to 3 show that as the pH went from acidic to basic to acidic again the percent transmission (%T) at 260 nm increased, then decreased, while the %T at 290 nm decreased, then increased. FIGS. 1 to 3 also show that the absorption can be measured at any wavelength between about 230 and about 270 and at any wavelength between about 280 and about 320, but that the maximum differences are at wavelengths of about 260 and about 290 nm.

EXAMPLE 3

Other base materials were also tried, including basic alumina, MgO, CaO, $CaCO_3$, triethanolamine, diethanolamine, and $NH_3OH$. All caused a change in the pattern, but not as pronounced as NaOH.

EXAMPLE 4

Figure 4:
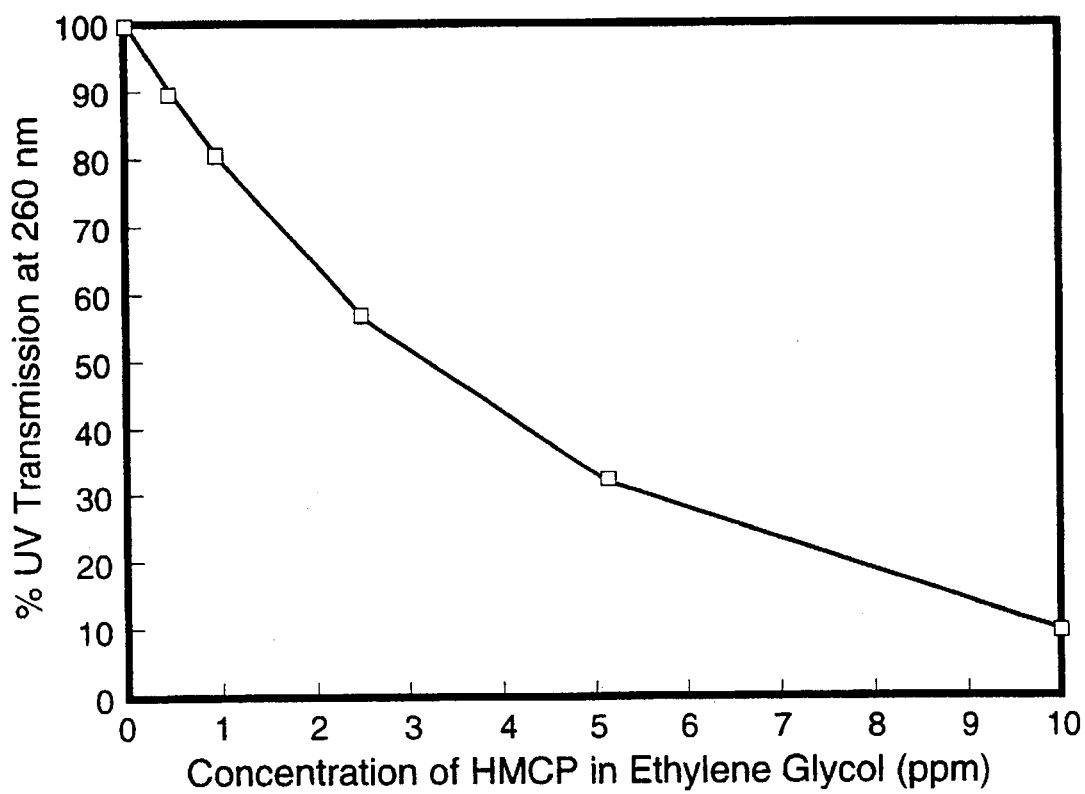
FIG. 4 is a calibration curve giving the percent UV transmission at 260 nm of various concentrations of the dione form of a cyclic dione in ethylene glycol.

The percent UV transmission in a 1 cm cell was measured at HMCP concentrations of 0, 0.5, 1, 2.5, 5, and 10 ppm at 260 nm. FIG. 4 gives the results, where the ordinate is percent transmission and the abscissa is HMCP concentration in ppm. FIG. 4 shows that UV transmission at 260 nm is depressed in the presence of HMCP.

EXAMPLE 5

A known amount of reagent grade 99% pure HMCP was spiked into distilled water to prepare standard solutions with HMCP concentrations ranging from 0.5 to 10.5 ppm. The UV absorbance at 260 and 290 nm was measured on these solutions, which had a pH of 4 to 5. The solutions were acidified to a pH of 1 to 2 using sulfuric acid before another measurement of UV absorbance was performed at 260 and 290 nm. The pH was increased to 12 using NaOH, and the UV absorbance again was measured. From the change of absorbance at 260 and 290 nm at each known HMCP concentration, the ratio of the concentration to the change in absorbance was the proportionality constant needed to determine an unknown sample. The average value of the proportionality constant was −11.9 ppm per absorbance unit at 260 nm and 13.8 ppm per absorbance unit at 290 nm, respectively. The data are shown below:

| | Absorbance at pH4–5 | | Absorbance at pH1–2 | | Absorbance to pH12 | | Change in Absorbance from pH1–2 to pH12 | | Ratio of ppm to Change in Absorbance | |
|---|---|---|---|---|---|---|---|---|---|---|
| HMCP ppm | 260 nm | 290 nm | 260 nm | 290 nm | 260 nm | 290 nm | 260 nm | 290 nm | 260 nm | 290 nm |
| 0.5 | .03 | .011 | .063 | .012 | .023 | .048 | −.040 | .036 | −12.5 | 13.9 |
| 1 | .071 | .026 | 0.112 | .009 | .027 | .087 | −.085 | .078 | −11.8 | 12.8 |
| 2.6 | .212 | .066 | 0.278 | .021 | .053 | .203 | −.225 | .182 | −11.6 | 14.3 |
| 5.2 | .392 | .159 | 0.545 | .039 | .101 | .413 | −.444 | .374 | −11.7 | 13.9 |
| 10.5 | .926 | .214 | 1.082 | .078 | .197 | .824 | −.885 | .746 | −11.9 | 14.1 |
| Average Proportionality Constant | | | | | | | | | −11.9 | 13.8 |

EXAMPLE 6

A solution containing 3 ppm of 1,3-cyclopentanedione was prepared in water having a pH between 5 and 6. A UV scan revealed an absorption maxima near 260 nm. When caustic was added to increase the pH to 12, there was no shift in the absorption maxima.

We claim:

1. A method of determining whether a solvent contains a tautomeric cyclic 1,2-dione comprising (A) determining if the pH of said solvent is acidic, basic, or neutral;

(B) if said pH is neutral, adding an acid or a base to make said pH acidic or basic, respectively;

(C) determining the UV absorbance at a first wavelength between about 230 nm and about 270 nm and at a second wavelength between about 280 nm and 320 nm;

(D) if said pH is acidic, changing the pH to basic or, if said pH is basic, changing said pH to acidic; and (E) determining the UV absorbance again at said first and second wavelengths, whereby the presence of a tautomeric cyclic 1,2-dione is indicated if the absorbance at said first wavelength is greater when said solvent is acidic and the absorbance at said second wavelength is greater when said solvent is basic.

2. A method according to claim 1 wherein said tautomeric cyclic 1,2-dione is 3-methyl-1, 2-cyclopentane dione.

3. A method according to claim 1 wherein said solvent is monoethylene glycol.

4. A method according to claim 3 wherein the concentration of said tautomeric cyclic 1,2-dione is about 0.1 to about 1 ppm.

5. A method according to claim 1 wherein said solvent is propylene glycol.

6. A method according to claim 1 wherein said solvent is diethylene glycol.

7. A method according to claim 1 wherein said acidic pH is <5, said basic pH is >9, and said neutral pH is 5 to 9.

8. A method according to claim 1 wherein said first wavelength is about 260 nm and said second wavelength is about 290 nm.

9. A method according to claim 1 wherein the change in absorbance at said first wavelength or at said second wavelength when said pH is changed is multiplied by a constant to determine the amount of said tautomeric cyclic 1,2-dione that is present.

10. A method of detecting the presence of about 0.1 to about 1 ppm of a tautomeric cyclic 1,2-dione in a solution of monoethylene glycol having a pH less than 5 comprising (A) measuring the UV absorbance at a first wavelength between about 230 and about 270 nm and at a second wavelength between about 280 and about 320 nm;

(B) changing the pH of said solution to greater than 9; and (C) measuring the UV absorbance again at said first wavelength and at said second wavelength, whereby the presence of said tautomeric cyclic 1,2-dione is indicated if said absorbance at said first wavelength is less in step (C) than in step (A) and said absorbance at said second wavelength is greater in step (C) than in step (A).

11. A method according to claim 10 wherein said tautomeric cyclic 1,2-dione is 3-methyl-1,2-cyclopentane dione.

12. A method according to claim 11 wherein said first wavelength is about 260 nm and said second wavelength is about 290 nm.

13. A method according to claim 12 wherein the concentration in ppm of said tautomeric cyclic 1,2-dione is determined by multiplying the change in absorbance at said first wavelength by about −11.9 or the change in absorbance at said second wavelength by about 13.8.

14. A method of determining the presence of about 0.1 to about 1 ppm of a tautomeric cyclic 1,2-dione in a solution of monoethylene glycol having a pH greater than 9 comprising (A) measuring the UV absorbance at a first wavelength between about 230 and about 270 nm and at a second wavelength between about 280 and about 320 nm;

(B) changing the pH of said solution to less than 5; and (C) measuring the UV absorbance again at said first wavelength and at said second wavelength, whereby the presence of said tautomeric cyclic 1,2-dione is indicated if said absorbance at said first wavelength is greater in step (A) than in step (C) and said absorbance at said second wavelength is less in step (A) than in step (C).

15. A method according to claim 14 wherein said tautomeric cyclic 1,2-dione is 3-methyl-1,2-cyclopentane dione.

16. A method according to claim 15 wherein said first wavelength is about 260 nm and said second wavelength is about 290 nm.

17. A method according to claim 16 wherein the concentration in ppm of said tautomeric cyclic 1,2-dione is determined by multiplying the change in absorbance at said first wavelength by about 11.9 or the change in absorbance at said second wavelength by about −13.8.

* * * * *